US008129312B2

(12) United States Patent
Berghaus et al.

(10) Patent No.: US 8,129,312 B2
(45) Date of Patent: Mar. 6, 2012

(54) USE OF DEFINED ALCOHOL ALKOXYLATES AS ADJUVANTS IN THE AGROTECHNICAL FIELD

(75) Inventors: Rainer Berghaus, Speyer (DE); Oskar Schmidt, Schifferstadt (DE); Harald Köhle, Bobenheim (DE); Reinhard Stierl, Freinsheim (DE); Norbert Wagner, Mutterstadt (DE); Paul Klingelhöfer, Mannheim (DE)

(73) Assignee: BASF SE, Ludwigshafen (DE)

(*) Notice: Subject to any disclaimer, the term of this patent is extended or adjusted under 35 U.S.C. 154(b) by 2200 days.

(21) Appl. No.: 10/512,422

(22) PCT Filed: Apr. 24, 2003

(86) PCT No.: PCT/EP03/04276

§ 371 (c)(1), (2), (4) Date: Oct. 25, 2004

(87) PCT Pub. No.: WO03/090531

PCT Pub. Date: Nov. 6, 2003

(65) Prior Publication Data

US 2005/0170968 A1 Aug. 4, 2005

(30) Foreign Application Priority Data

Apr. 24, 2002 (DE) .................................. 102 18 316

(51) Int. Cl.

| | |
|---|---|
| ***A01N 25/00*** | (2006.01) |
| ***A01N 57/18*** | (2006.01) |
| ***A01N 43/72*** | (2006.01) |
| ***A01N 43/40*** | (2006.01) |
| ***A01N 41/06*** | (2006.01) |
| ***A01N 25/02*** | (2006.01) |

(52) U.S. Cl. ..................... 504/116.1; 504/206; 504/222; 504/250; 504/333; 504/362

(58) Field of Classification Search ............... 504/116.1, 504/206, 222, 250, 333, 362, 975

See application file for complete search history.

(56) References Cited

U.S. PATENT DOCUMENTS

| | | | | |
|---|---|---|---|---|
| 5,427,795 | A | 6/1995 | Feyen et al. | |
| 5,661,121 | A * | 8/1997 | Dahlgren et al. | 510/245 |
| 6,057,284 | A | 5/2000 | Baur et al. | |
| 6,117,820 | A * | 9/2000 | Cutler et al. | 504/206 |
| 6,124,301 | A | 9/2000 | Aven et al. | |
| 6,680,412 | B2 | 1/2004 | Guembel et al. | |
| 2003/0092587 | A1 | 5/2003 | Gumbel et al. | |
| 2008/0064756 | A1 | 3/2008 | Berghaus et al. | 514/617 |

FOREIGN PATENT DOCUMENTS

| | | | |
|---|---|---|---|
| CA | 2683034 | | 11/2008 |
| EP | 0 356 812 | B1 | 3/1990 |
| EP | 0 473 003 | A2 | 3/1992 |
| EP | 0 906 150 | B1 | 4/1999 |
| WO | WO 95/18531 | | 7/1995 |
| WO | WO 96/31121 | | 10/1996 |
| WO | WO 97/00010 | | 1/1997 |
| WO | WO 97/46311 | | 12/1997 |
| WO | WO 99/03345 | * | 1/1999 |
| WO | WO 00/42847 | | 7/2000 |
| WO | WO 01/30147 | A1 | 5/2001 |
| WO | WO 01/77276 | | 10/2001 |
| WO | WO 02/15697 | | 2/2002 |
| WO | WO 2005/015998 | | 2/2005 |
| WO | WO 2008/132150 | | 11/2008 |
| WO | WO 2009/013247 | | 1/2009 |
| WO | WO 2009/130281 | | 10/2009 |

OTHER PUBLICATIONS

Stoesser et al. U.S. Appl. No. 12/597,043 (00000 59058) "Alcohol alkoxylates, compositions containing these, and use of the alcohol alkoxylates as adjuvants for the agrochemical field".

Stoesser et al. U.S. Appl. No. 12/669,215 (PF 00000 60018) "Compositions comprising alcohol alkoxylates, and use of the alcohol alkoxylates as adjuvants for the agrochemical sector".

* cited by examiner

*Primary Examiner* — Johann Richter
*Assistant Examiner* — Luke Karpinski
(74) *Attorney, Agent, or Firm* — Novak Druce + Quigg LLP

(57) ABSTRACT

The present invention relates to the use of specific amphiphilic alkoxyates as synergistic adjuvant for agrotechnical applications. Suitable agrotechnical compositions are also described. Thus, the addition of such alkoxylates makes possible an accelerated uptake of active ingredients by the plant.

The alkoxylates to be used are alkoxylates based on branched alcohols such as 2-propylheptanol, $C_{13}$-oxo alcohols and $C_{10}$-oxo alcohols.

30 Claims, No Drawings

USE OF DEFINED ALCOHOL ALKOXYLATES AS ADJUVANTS IN THE AGROTECHNICAL FIELD

The present invention relates to the use of specific amphiphilic alcohol alkoxylates as synergistic adjuvant for agrotechnical applications, in particular in the field of crop protection. Suitable agrotechnical compositions are also described.

An important factor with a view to industrial production and application of active ingredients is, besides the optimization of the active ingredient's properties, the development of an efficacious composition. The expert formulation of the active ingredient(s) has the task of creating an ideal balance between properties such as bioactivity, toxicology, possible effects on the environment and costs, some of which are contrary. Moreover, the shelf life and the user friendliness of a composition is to a high degree determined by the formulation.

An aspect which is of particular importance for the activity of an agrotechnical composition is the effective uptake of the active ingredient by the plant. If uptake is via the leaf, a complex transport process results, in which the load of active ingredient, for example herbicide, must first penetrate the waxy cuticle of the leaf and must subsequently diffuse, via the cuticle, to the actual site of action in the subjacent tissue.

The addition to formulations of certain auxiliaries in order to improve the activity is generally known and agricultural practice. This has the advantage that the amounts of active ingredient in the formulation can be reduced while maintaining the activity of the latter, thus allowing costs to be kept as low as possible and any official regulations to be followed. In individual cases it is also possible to widen the spectrum of action since plants where the treatment with a particular active ingredient without addition was insufficiently successful can indeed be treated successfully by the addition of certain auxiliaries. Moreover, the performance may be increased in individual cases by a suitable formulation when the environmental conditions are not favorable. The phenomenon that various active ingredients are not compatible with each other in a formulation can therefore also be avoided.

Such auxiliaries are generally also referred to as adjuvants. Frequently, they take the form of surface-active or salt-like compounds. Depending on their mode of action, they can roughly be classified as modifiers, actuators, fertilizers and pH buffers.

Modifiers affect the wetting, sticking and spreading properties of a formulation. Actuators break up the waxy cuticle of the plant and improve the penetration of the active ingredient into the cuticle, both short-term (over minutes) and long-term (over hours). Fertilizers such as ammonium sulfate, ammonium nitrate or urea improve the absorption and solubility of the active ingredient and may reduce the antagonistic behavior of active ingredients. pH buffers are conventionally used for bringing the formulation to an optimal pH.

Regarding the uptake of the active ingredient into the leaf, surface-active substances may act as modifiers and actuators. In general, it is assumed that suitable surface-active substances can increase the effective contact area of liquids on leaves by reducing the surface tension. Moreover, surface-active substances can dissolve or break up the epicuticular waxes, which facilitates the absorption of the active ingredient. Furthermore, some surface-active substances can also improve the solubility of active ingredients in formulations and thus avoid, or at least delay, crystallization. Finally, they can also affect the absorption of active ingredients in some cases by retaining moisture.

Surfactant-type adjuvants are exploited in a number of ways for agrotechnical applications. They can be divided into groups of anionic, cationic, nonionic or amphoteric substances.

Substances which are traditionally used as activating adjuvants are petroleum-based oils. More recently, seed extracts, natural oils and their derivatives, for example of soybeans, sunflowers and coconut, have also been employed.

Synthetic surface-active substances which are conventionally used as actuators take the form of, inter alia, polyoxyethylene condensates with alcohols, alkylphenols or alkylamines with HLB values in the range of from 8 to 13. In this context WO 00/42847, for example, mentions the use of specific linear alcohol alkoxylates in order to increase the activity of agrotechnical biocide formulations. EP-A 0 356 812 describes adjuvants which are said to comprise not only an anionic surfactant, but also a nonionic surfactant. Nonionic surfactants which are considered suitable are polyalkoxylated $C_6$-$C_{22}$-alkyl ethers.

However, the alcohol alkoxylates cover a wide spectrum. As surfactants, they are predominantly used in cleaners and detergents, in the metalworking industry, in the production and processing of textiles, in the leather industry, in papermaking, in the printing industry, in the electroplating industry and in the photographic industry, in the treatment of water, in pharmaceutical formulations, formulations for veterinary use and crop protection formulations, or in the polymer-producing and -processing industries. In particular the structures of the alcohol moiety, and in some cases also of the alkoxylate moiety, affect the properties of the alkoxylates, so that various technical effects can be exploited in the abovementioned applications. These include wetting, spreading, penetration, adhesion, film formation, the improvement of compatibilities, drift control and defoaming.

Thus, for example, WO 01/77276, U.S. Pat. No. 6,057,284 and U.S. Pat. No. 5,661,121 describe certain alcohol alkoxylates as foam-reducing surfactants. These surfactants are block alkoxylates whose alcohol moiety is branched.

It is an object of the present invention to provide further uses of such alkoxylates which are based on branched alcohols.

We have found that this object is achieved by using the alkoxylates as adjuvant and by providing agrotechnical compositions comprising these alkoxylates.

The present invention therefore relates to the use of at least one alkoxylated branched alcohol as adjuvant in the treatment of plants.

The alkoxylates to be used in accordance with the invention have adjuvant, in particular synergistic, properties. Thus, the addition of such alkoxylates makes possible an accelerated uptake of active ingredients by a plant to be treated with the active ingredient. The adjuvant action results in particular in the following aspects in the treatment of plants with one or more active ingredients:

- in comparison higher activity of the active ingredient for a given application rate;
- in comparison lower application rate with a given effect;
- in comparison better uptake of the active ingredient by the plant, in particular via the leaf, and thus advantages for the post-emergence treatment, in particular the spray treatment of plants.

The use according to the invention aims in particular at plant cultivation, agriculture and horticulture. It is intended in particular for controlling undesired plant growth.

Accordingly, the present invention also relates to methods, for the treatment of plants, which correspond to the above intended uses, a suitable amount of alkoxylate according to the invention being applied.

Particular advantages are achieved in particular in the production of *Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum*, (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N. rustica*), *Olea europaea, Oryza sativa, Phaseolus lunatus, Phaseolus vulgaris, Picea abies, Pinus* spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera, Zea mays.*

In addition, the alkoxylates to be used in accordance with the invention may also be used in crops which tolerate the effect of herbicides. Such crops can be obtained for example by breeding and also by recombinant methods.

At least some of the alkoxylates to be used are known per se. For example WO 01/77276 and U.S. Pat. No. 6,057,284 or EP 0 906 150 describe suitable alkoxylates. The description of these alkoxylates in these publications is herewith expressly referred to, whereby the alkoxylates themselves which are disclosed therein and also their preparation are incorporated into the present disclosure.

As a rule, the alcohol moiety of the alcohol alkoxylates to be used in accordance with the invention is based on alcohols or alcohol mixtures known per se which have 5 to 30, preferably 8 to 20, in particular 10 to 13, carbon atoms. Fatty alcohols having approximately 8 to 20 carbon atoms must be mentioned in particular. As is known, many of these fatty alcohols are employed in the production of nonionic and anionic surfactants, to which end the alcohols are subjected to suitable functionalization, for example by alkoxylation or glycosidation.

The alcohol moiety of the alkoxylates to be used is branched. Thus, the main chain of the alcohol moiety has, as a rule, 1 to 4 branchings, it also being possible to use alcohols with a higher or lower degree of branching in a mixture with other alcohol alkoxylates as long as the mean number of branchings of the mixture is in the above-stated range.

In general, the branchings independently of one another have 1 to 10, preferably 1 to 6, in particular 1 to 4, carbon atoms. Particular branchings are methyl, ethyl, n-propyl or isopropyl groups.

In accordance with one embodiment, the alcohol moieites on which the alkoxylates are based thus have an average of at least two terminal methyl groups.

Suitable alcohols and, in particular, fatty alcohols are obtainable both from natural sources, for example by obtaining and, if required or desired, by hydrolyzing, transesterifying and/or hydrogenating glycerides and fatty acids, and by synthetic routes, for example by building up from starting materials having a smaller number of carbon atoms. Thus, for example, the SHOP process (Shell Higher Olefin Process) gives, starting from ethene, olefin fractions having a number of carbon atoms suitable for further processing to produce surfactants. The functionalization of the olefins to form the corresponding alcohols is carried out, for example, by hydroformylation and hydrogenation.

Olefins having a number of carbon atoms suitable for further processing to give suitable alcohols can also be obtained by oligomerization of $C_3$-$C_6$-alkenes, in particular propene or butene or mixtures of these.

Moreover, lower olefins can be oligomerized by means of heterogeneous, acidic catalysts, e.g. supported phosphoric acid, and subsequently functionalized to give alcohols.

A general possibility of synthesizing to produce branched alcohols is, for example, the reaction of aldehydes or ketones with Grignard reagents (Grignard synthesis). Instead of Grignard reagents, it is also possible to employ aryllithium or alkyllithium compounds, which are distinguished by higher reactivity. Moreover, the branched alcohols can be obtained by aldol condensation, the skilled worker being familiar with the reaction conditions.

The alkoxylation is the result of the reaction with suitable alkylene oxides which, as a rule, have 2 to 15, preferably 2 to 6, carbon atoms. The following may be mentioned in particular in this context: ethylene oxide (EO), propylene oxide (PO), butylene oxide (BO), pentylene oxide (PeO) and hexylene oxide (HO).

One type of alcohol alkoxylate to be used is based on one type of alkylene oxide.

A further type of alcohol alkoxylate to be used is based on at least two different types of alkylene oxide. It is preferred in this context to arrange several alkylene oxide units of one type as a block, resulting in at least two different alkylene oxide blocks, each of which is formed by several units of identical alkylene oxides. If such block alkoxylates are used, it is preferred that the alkylene oxide moiety is composed of 3, in particular 2, blocks.

According to one aspect, it is preferred that the alcohol alkoxylates to be used in accordance with the invention are ethoxylated or have at least one ethylene oxide block. According to a further aspect, ethylene oxide blocks are combined in particular with propylene oxide blocks or pentylene oxide blocks.

The respective degree of alkoxylation is a function of the amounts of alkylene oxide(s) chosen for the reaction and the reaction conditions. It is, as a rule, a statistic mean since the number of alkylene oxide units of the alcohol alkoxylates resulting from the reaction varies.

The degree of alkoxylation, i.e. the mean chain length of the polyether chains of alcohol alkoxylates to be used in accordance with the invention, can be determined by the molar ratio of alcohol to alkylene oxide. Preferred alcohol alkoxylates are those having approxiamtely 1 to 100, preferably approximately 2 to 15, in particular 3 to 12, mainly 4 to 12 and especially 5 to 12 alkylene oxide units.

The alcohols, or alcohol mixtures, are reacted with the alkylene oxide(s) by customary methods with which the skilled worker is familiar and in apparatuses conventionally used for this purpose.

The alkoxylation may be catalyzed by strong bases such as alkali metal hydroxides and alkaline earth metal hydroxides, Brönsted acids or Lewis acids, such as $AlCl_3$, $BF_3$ and the like. Catalysts such as hydrotalcite or DMC may be used for alcohol oxylates with a narrow distribution.

The alkoxylation is preferably carried out at temperatures in the range of from approximately 80 to 250° C., preferably approximately 100 to 220° C. The pressure range is preferably between atmospheric pressure and 600 bar. If desired, the alkylene oxide may comprise an admixture of inert gas, for example of from approximately 5 to 60%.

Accordingly, the alkoxylated branched alcohols to be used are selected in particular among alcohol alkoxylates of the formula (I)

$$R—O—(C_mH_{2m}O)_x—(C_nH_{2n}O)_y—(C_pH_{2p}O)_z—H \quad (I)$$

in which

R is branched $C_5$-$C_{30}$-alkyl;

m, n, p independently of one another are an integer from 2 to 16, preferably 2, 3, 4 or 5;

x+y+z have a value of 1 to 100, and the embodiments of alcohol alkoxylates of the formula (I) which result taking into consideration what has been said above.

In accordance with a particular embodiment, alcohol alkoxylates of the formula (I) are used in which m=2 and the value of x is greater than zero. These are alcohol alkoxylates of the EO type, which include mainly alcohol ethoxylates (m=2; x>zero; y, z=zero) and alcohol alkoxylates with an EO block bonded to the alcohol moiety (m=2; x>zero; y and/or z>zero). Substances which must be mentioned among the alcohol alkoxylates with an EO block bonded to the alcohol moiety are mainly EO/PO block alkoxylates (m=2; x>zero; y>zero; n=3; z=0), EO/PeO block alkoxylates (m=2; x>zero; y>zero; n=5; z=0) and EO/PO/EO block alkoxylates (m, p=2; x, z>zero; y>zero; n=3).

Preferred substances are EO/PO block alkoxylates in which the EO:PO ratio (x:y) is 1:1 to 4:1, in particular 1.5:1 to 3:1. In this context, the degree of ethoxylation (value of x) is, as a rule, 1 to 20, preferably 2 to 15, in particular 4 to 10, and the degree of propoxylation (value of y) is, as a rule, 1 to 20, preferably 1 to 8, in particular 2 to 5. The total degree of alkoxylation, i.e. the total of EO and PO units, is, as a rule, 2 to 40, preferably 3 to 25, in particular 6 to 15.

Furthermore preferred are EO/PeO block alkoxylates in which the EO:PeO ratio (x:y) is 2:1 to 25:1, in particular 4:1 to 15:1. In this context, the degree of ethoxylation (value of x) is, as a rule, 1 to 50, preferably 4 to 25, in particular 6 to 15, and the degree of pentoxylation (value of y) is, as a rule, 0.5 to 20, preferably 0.5 to 4, in particular 0.5 to 2. The total degree of alkoxylation, i.e. the total of EO and PeO units, is, as a rule, 1.5 to 70, preferably 4.5 to 29, in particular 6.5 to 17.

In accordance with a further particular embodiment, alcohol alkoxylates of the formula (I) are used in which n=2, the values of x and y are both greater than zero and z=0. Again, these alcohol alkoxylates take the form of the EO type, with the EO block being bonded terminally, however. These include mainly PO/EO block alkoxylates (n=2; x>zero; y>zero; m=3; z=0) and PeO/EO block alkoxylates (n=2; x>zero; y>zero; m=5; z=0).

Preferred PO/EO block alkoxylates are those in which the PO:EO ratio (x:y) is 1:10 to 3:1, in particular 1.5:1 to 1:6. In this context, the degree of ethoxylation (value of y) is, as a rule, 1 to 20, preferably 2 to 15, in particular 4 to 10, and the degree of propoxylation (value of x) is, as a rule, 0.5 to 10, preferably 0.5 to 6, in particular 1 to 4. The total degree of alkoxylation, i.e. the total of EO and PO units, is, as a rule, 1.5 to 30, preferably 2.5 to 21, in particular 5 to 14.

Furthermore preferred are PeO/EO block alkoxylates in which the PeO:EO ratio (x:y) is 1:50 to 1:3, in particular 1:25 to 1:5. In this context, the degree of pentoxylation (value of x) is, as a rule, 0.5 to 20, preferably 0.5 to 4, in particular 0.5 to 2, and the degree of ethoxylation (value of y) is, as a rule, 3 to 50, preferably 4 to 25, in particular 5 to 15. The total degree of alkoxylation, i.e. the total of EO and PeO units, is, as a rule, 3.5 to 70, preferably 4.5 to 45, in particular 5.5 to 17.

In accordance with a further particular embodiment, alcohol alkoxylates of the formula (I) are used in which the values of x, y and z are all greater than zero. These include mainly PeO/EO/PO block alkoxylates (m=5; x>zero; n=2; y>zero; m=3; z>zero).

In accordance with a preferred embodiment, the alcohol alkoxylates to be used in accordance with the invention are based on primary, α-branched alcohols of the formula (II)

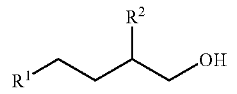

in which $R^1$, $R^2$ independently of one another are hydrogen or $C_1$-$C_{26}$-alkyl.

Preferably, $R^1$ and $R^2$ independently of one another are $C_1$-$C_6$-alkyl, in particular $C_2$-$C_4$-alkyl.

Very especially preferred are alcohol alkoxylates which are based on 2-propylheptanol. These include, in particular, alcohol alkoxylates of the formula (I) in which R is a 2-propylheptyl radical, i.e. $R^1$ and $R^2$ in formula (II) are in each case n-propyl.

Such alcohols are also referred to as Guerbet alcohols. They can be obtained for example by dimerization of corresponding primary alcohols (for example $R^{1,2}$ $CH_2CH_2OH$) at elevated temperature, for example 180 to 300° C., in the presence of an alkaline condensing agent such as potassium hydroxide.

Alkoxylates which are employed for the purposes of this preferred embodiment, which is based on Guebert alcohols, are mainly alkoxylates of the EO type. Particularly preferred are ethoxylates with a degree of ethoxylation of 1 to 50, preferably 2 to 20, in particular approximately 3 to 10. The correspondingly ethoxylated 2-propylheptanols may be mentioned especially among these.

In accordance with a further preferred embodiment, the alcohol alkoxylates to be used are based on $C_{13}$-oxo alcohols.

As a rule, the term "$C_{13}$-oxo alcohol" refers to an alcohol mixture whose main component is formed by at least one branched $C_{13}$-alcohol (isotridecanol). Such $C_{13}$-alcohols include, in particular, tetramethylnonanols, for example 2,4,6,8-tetramethyl-1-nonanol or 3,4,6,8-tetramethyl-1-nonanol and furthermore ethyldimethylnonanols such as 5-ethyl-4,7-dimethyl-1-nonanol.

Suitable $C_{13}$-alcohol mixtures can generally be obtained by hydrogenation of hydroformylated trimeric butene. In particular, it is possible to proceed as follows:

a) butenes are brought into contact with a suitable catalyst for oligomerization, b) a $C_{12}$-olefin fraction is isolated from the reaction mixture, c) the $C_{12}$-olefin fraction is hydroformylated by reacton with carbon monoxide and hydrogen in the presence of a suitable catalyst, and d) hydrogenated.

Advantageous $C_{13}$-alcohol mixtures are essentially free from halogens, i.e. they contain less than 3 ppm by weight, in particular less than 1 ppm by weight, of halogen, in particular chlorine.

The butene trimerization can be carried out with homogeneous or heterogeneous catalysis.

In the DIMERSOL process (cf. Revue de l'Institut Français du Petrole, Vol. 37, No. 5, September/October 1982, pp. 639ff), butenes are oligomerized in a homogeneous phase in the presence of a catalyst system comprising a transition metal derivative and an organometallic compound. Typical catalyst systems are Ni(O) complexes in combination with Lewis acids such as $AlCl_3$, $BF_3$, $SbF_5$ and the like, or Ni(II) complexes in combination with alkylaluminum halides.

However, it is also possible to oligomerize butenes in the manner known per se using a heterogeneous nickel-containing catalyst (process step a). Depending on the selected reaction conditions, different relative amounts of butene dimers, trimers and higher oligomers are obtained. The butene trimers, i.e. $C_{12}$-olefins, are further processed for the present purposes. The isobutene content may be selected with a view to the desired degree of branching of the $C_{13}$-alcohol mixture obtained after the hydroformylation/-hydrogenation. Relatively low degrees of branching require a relatively low isobutene content and vice versa. If, for example, the $C_{12}$-olefin fraction is to have an ISO index of approximately 1.9 to 2.3, it is expedient to select predominantly linear butenes, i.e. the hydrocarbon stream which is generally employed should contain less than 5% by weight of isobutene based on the butene fraction. The butenes may contain an admixture of saturated $C_4$-hydrocarbons, which act as diluent in the oligomerization process.

The heterogeneous nickel-containing catalysts which may be used can have different structures, with catalysts containing nickel oxide being preferred. Catalysts which are known per se as described in C. T. O'Connor et al., Catalysis Today, vol. 6 (1990), pp. 336-338 are suitable.

The hydrocarbon stream (preferably $C_4$) comprises, as a rule, from 50 to 100% by weight, preferably from 60 to 90% by weight, of butenes and from 0 to 50% by weight, preferably from 10 to 40% by weight, of butanes. The butene fraction contains less than 5% by weight, in particular less than 3% by weight, of isobutene, based on the butene fraction. The butene fraction generally has the following composition (in each case based on the butene fraction):

| | |
|---|---|
| 1-butene | 1 to 50% by weight |
| cis-2-butene | 1 to 50% by weight |
| trans-2-butene | 1 to 99% by weight |
| isobutene | 1 to 5% by weight |

A particularly preferred starting material which is employed is what is known as raffinate II, which is an isobutene-depleted $C_4$ fraction from an FCC plant or a steam cracker.

Starting with the material obtained in the oligomerization reaction, a $C_{12}$-olefin fraction is isolated in one or more separation steps (process step b). Suitable separation devices are the usual apparatuses familiar to the skilled worker. These include, for example, distillation columns such as tray columns which may, if desired, be equipped with bubble caps, sieve plates, sieve trays, valves, side offtakes and the like, evaporators such as thin-film evaporators, falling-film evaporators, wiper-blade evaporators, Sambay evaporators and the like, and combinations thereof. The $C_{12}$-olefin fraction is preferably isolated by fractional distillation.

The ISO index of the $C_{12}$-olefin fraction, which indicates the mean number of branchings, is generally from 1 to 4, preferably 1.9 to 2.3, in particular 2.0 to 2.3. The ISO index can be determined, for example, by hydrogenating a sample of the $C_{12}$-olefin fraction to give the dodecanes and determining the mean number of methyl groups with the aid of the signal area attributable to the methyl groups and the signal area attributable to the total of the protons in the $^1$H-NMR spectrum. The ISO index is the mean number of methyl groups minus two.

To prepare an alcohol mixture according to the invention, the $C_{12}$-olefin fraction which has been isolated is hydroformylated to give $C_{13}$-aldehydes (process step c), and these are subsequently hydrogenated to form $C_{13}$-alcohols (process step d). The preparation of the alcohol mixture can be carried out in a single step or in two separate reaction steps.

An overview of hydroformylation processes and suitable catalysts can be found in Beller et al., Journal of Molecular Catalysis A 104 (1995), pp. 17-85.

The hydroformylation is preferably carried out in the presence of a cobalt hydroformylation catalyst. The amount of the hydroformylation catalyst is generally from 0.001 to 0.5% by weight, calculated as cobalt metal and based on the amount of the olefins to be hydroformylated. The reaction temperature is generally in the range of from about 100 to 250° C., preferably from 150 to 210° C. The reaction may be carried out at a superatmospheric pressure of from about 10 to 650 bar. The hydroformylation is preferably carried out in the presence of water; however, it may also be carried out in the absence of water.

Carbon monoxide and hydrogen are usually used in the form of a mixture known as synthesis gas. The composition of the synthesis gas employed can vary within a wide range. The molar ratio of carbon monoxide to hydrogen is generally from approximately 2.5:1 to 1:2.5. A preferred ratio is about 1:1.5.

The cobalt catalyst which is dissolved homogeneously in the reaction medium can be separated from the hydroformylation product in a suitable manner by treating the reaction product of the hydroformylation process with oxygen or air in the presence of an acidic aqueous solution. This destroys the cobalt catalyst by oxidation to give cobalt(II) salts. The cobalt (II) salts are water-soluble and are extracted into the aqueous phase, which can be separated off and returned to the hydroformylation process.

The crude aldehydes or aldehyde/alcohol mixtures obtained in the hydroformylation can, if desired, be isolated before hydrogenation by customary methods known to the skilled worker and, if appropriate, purified.

For the hydrogenation, the reaction mixtures obtained in the hydroformylation are reacted with hydrogen in the presence of hydrogenation catalysts.

Suitable hydrogenation catalysts are generally transition metals such as, for example, Cr, Mo, W, Fe, Rh, Co, Ni, Pd, Pt, Ru and the like or mixtures of these, which may be applied to supports such as active charcoal, aluminum oxide, kieselguhr and the like, to increase activity and stability. To increase the catalytic activity, it is possible to use Fe, Co and, preferably, Ni as metal sponge having a very high surface area, including these metals in the form of the Raney catalysts. A Co/Mo catalyst is preferably employed for the preparation of the surfactant alcohols according to the invention. Depending on the activity of the catalyst, the oxo aldehydes are preferably hydrogenated at elevated temperatures and superatmospheric pressures. The hydrogenation temperature is preferably at about 80 to 250° C., and the pressure is preferably at approximately 50 to 350 bar.

Further suitable $C_{13}$-alcohol mixtures can be obtained by proceeding as follows:

a) subjecting a $C_4$-olefin mixture to metathesis, b) separating olefins having 6 C atoms from the metathesis mixture, c) subjecting the olefins which have been separated off, individually or as a mixture, to a dimerization to give olefins mixtures having 12 C atoms, and d) subjecting the resulting olefin mixture, if appropriate after fractionation, to derivatization to give a $C_{13}$-oxo alcohol mixture.

The principles of the metathesis employed in process step a) have been described for example in Ullmann's Ecyclopedia of Industrial Chemistry, 5th Ed., Vol. A18, pp. 235/236. More information on how this process is carried out can be found in, for example, K. J. Ivin, "Olefin Metathesis, Academic Press, London, (1983); Houben-Weyl, E18, 1163-1223; R. L. Banks, Discovery and Development of Olefin Disproportionation, CHEMTECH (1986), February, 112-117.

When applying metathesis to the main constituents but-1-ene and but-2-ene present in the $C_4$-olefin streams, olefins having 5 to 10 C atoms, preferably 5 to 8 C atoms, but in particular pent-2-ene and hex-3-ene, are formed in the presence of suitable catalysts.

Suitable catalysts are preferably molybdenum, tungsten or rhenium compounds. It is particularly expedient to carry out the reaction with heterogeneous catalysis, the catalytically active metals being employed in particular with $Al_2O_3$ or $SiO_2$ supports. Examples of such catalysts are $MoO_3$ or $WO_3$ on $SiO_2$, or $Re_2O_7$ on $Al_2O_3$.

It is particularly advantageous to carry out the metathesis in the presence of a rhenium catalyst, since this allows particularly mild reaction conditions to be used. Thus, the metathesis may be carried out in this case at a temperature of from 0 to 50° C. and at low pressures of from approx. 0.1 to 0.2 MPa.

The dimerization of the olefins or olefin mixtures obtained in the metathesis step gives dimerization products which have particularly favorable components and a particularly advantageous compositions with a view to further processing into surfactant alcohols when a dimerization catalyst is employed which contains at least one element from group VIIIb of the Periodic Table and when the catalyst composition and the reaction conditions are chosen in such a way that a dimer mixture is obtained with less than 10% by weight of compounds which contain a structural element of the formula III (vinylidene group)

(III)

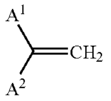

where $A^1$ and $A^2$ are aliphatic hydrocarbon radicals.

The internal linear pentenes and hexenes present in the metathesis product are preferably employed for the dimerization reaction. The use of hex-3-ene is particularly preferred.

The dimerization reaction can be carried out with homogeneous or heterogeneous catalysis. The heterogeneous procedure is preferred for two reasons, firstly because separation of the catalyst is simplified, thus making the procedure more economical, and secondly because no polluting wastewaters as are usually obtained when separating off dissolved catalysts, for example by hydrolysis, are generated. A further advantage of the heterogeneous procedure is the fact that the dimerization product contains no halogens, in particular chlorine or fluorine. Homogeneously soluble catalysts generally contain halide-containing ligands or are employed in combination with halogen-containing cocatalysts. Halogen from such catalyst systems may be incorporated into the dimerization products, which has a considerable adverse effect not only on product quality, but also on further processing steps, in particular the hydroformylation to give surfactant alcohols.

The heterogeneous catalysis expediently involves the use of combinations of oxides of metals of group VIIIb with aluminum oxide on support materials made of silicon oxides and titanium oxides as are known, for example, from DE-A-43 39 713. The heterogeneous catalyst may be employed in a solid bed, in which case it is preferably coarsely particulate as pellets of 1 to 1.5 mm, or in suspension (particle size 0.05 to 0.5 mm). When following the heterogeneous route, the dimerization is preferably carried out in a closed system at temperatures of from 80 to 200° C., preferably from 100 to 180° C., under the pressure which prevails at the reaction temperature or, if appropriate, under protective gas at superatmospheric pressure. To obtain optimum conversion rates, the reaction mixture is circulated repeatedly, a particular proportion of the circulating product continuously being drawn off and replaced by starting material.

The dimerization gives mixtures of monounsaturated hydrocarbons, with the chain lengths of the components being predominantly twice that of the starting olefins.

The dimerization catalysts and reaction conditions are expediently chosen in such a way within the context of what has been said that at least 80% of the components of the dimerization mixture have one branching, or two branchings at adjacent C atoms, over ¼ to ¾, preferably ⅓ to ⅔, of the chain length of their main chain.

The high percentage—as a rule more than 75%, in particular more than 80%—of components with branchings and the low percentage—as a rule less than 25%, in particular less than 20%—of unbranched olefins is highly characteristic of the olefin mixtures thus produced. A further characteristic is that predominantly groups with (y−4) and (y−5) C atoms are bonded to the branching sites of the main chain, y being the number of carbon atoms of the monomer employed in the dimerization process. The value (y−5)=0 means that no side chain is present.

The main chain of the $C_{12}$-olefin mixtures thus prepared preferably has methyl or ethyl groups at the branching points.

The position of the methyl and ethyl groups on the main chain is also characteristic. In the case of monosubstitution, the methyl or ethyl groups are in position P=(n/2)−m of the main chain, n being the length of the main chain and m the number of carbon atoms of the side groups, while in the case of disubstitution products one substituent is located at position P and the other at the adjacent carbon atom P+1. The percentages of monosubstitution products (single branching) in the olefin mixture prepared in accordance with the invention are characteristically all in the range of from 40-75% by weight, and the percentages of doubly branched components is in the range of from 5 to 25% by weight.

It has furthermore been found that the dimerization mixtures are particularly accessible to further derivatization when the position of the double bond meets certain requirements. In these advantageous olefin mixtures, the position of the double bonds relative to the branchings is characterized in that the ratio of the "aliphatic" hydrogen atoms to "olefinic" hydrogen atoms is in the range $H_{aliph.}:H_{olefin.}=(2*n-0.5):0.5$ to $(2*n-1.9):1.9$, n being the number of carbon atoms of the olefin resulting from the dimerization process.

(Hydrogen atoms referred to as "aliphatic" are hydrogen atoms which are bonded to carbon atoms which do not form part of a C═C-double bond (Pi bond), while "olefinic" hydrogen atoms are those which are bonded to a carbon atom which actuates a Pi bond).

Especially preferred dimerization mixtures are those in which the ratio $$H_{aliph.}:H_{olefin.}=(2*n-1.0):1 \text{ to } (2*n-1.6):1.6.$$

The olefin mixtures thus produced are first hydroformylated by reaction with carbon monoxide and hydrogen in the presence of suitable catalysts, preferably cobalt- or rhodium-containing catalysts, to give surfactant alcohols (oxo alcohols), branched primary alcohols.

A good overview of the method of hydroformylation, including a number of further references, can be found for example in the comprehensive essay by Beller et al. in Journal of Molecular Catalysis, A104 (1995) 17-85 or in Ullmanns Encyclopedia of Industrial Chemistry, Vol. A5 (1986), page 217 ff., page 333, and the literature referred to.

Owing to the comprehensive information provided therein, it is possible for the skilled worker also to hydroformylate the branched olefins according to the invention. In this reaction, CO and hydrogen undergo an addition reaction with olefinic double bonds, giving rise to mixtures of aldehydes and alkanols as shown in the reaction scheme below:

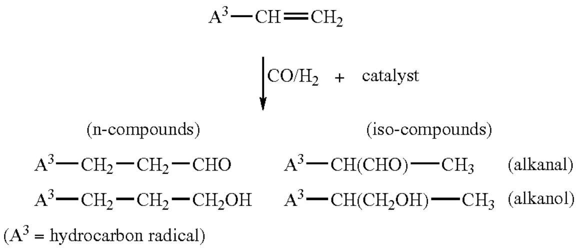

The molar ratio of n- and iso-compounds in the reaction mixture is usually in the range of from 1:1 to 20:1, depending on the selected process conditions for the hydroformylation and the catalyst employed. The hydroformylation is usually carried out in the temperature range of from 90 to 200° C. and at a $CO/H_2$ pressure of from 2.5 to 35 MPa (25 to 350 bar). The mixing ratio of carbon monoxide to hydrogen depends on whether the reaction is intended to yield predominantly alkanals or alkanols. The process is expediently carried out in a CO:H range of from 10:1 to 1:10, preferably 3:1 to 1:3, the range of the lower partial pressures of hydrogen being selected if alkanals are to be prepared and the range of the higher partial pressures of hydrogen, for example $CO:H_2=1:2$, being chosen if alkanols are to be prepared.

Suitable catalysts are, mainly, metal compounds of the general formula $HM(CO)_4$ or $M_2(CO)_8$ where M is a metal atom, preferably a cobalt, rhodium or ruthenium atom.

In general, the catalysts or catalyst precursors employed in each case give, under hydroformylation conditions, catalytically active species of the general formula $H_xM_y(CO)_zL_q$ in which M is a metal of group VIIIb, L is a ligand which may be a phosphine, phosphite, amine, pyridine or any other donor compound, also in polymeric form, and q, x, y and z are integers which depend on the valency and type of the metal and on the binding ability of the ligand L, it also being possible for q to be 0.

The metal M is preferably cobalt, ruthenium, rhodium, palladium, platinum, osmium or iridium, in particular cobalt, rhodium or ruthenium.

Examples of suitable rhodium compounds or complexes are rhodium(II) and rhodium(III) salts such as rhodium(III) chloride, rhodium(III) nitrate, rhodium(III) sulfate, potassium rhodium sulfate, rhodium(II) carboxylate, rhodium(III) carboxylate, rhodium(II) acetate, rhodium(III) acetate, rhodium(III) oxide, salts of rhodic(III) acid, such as, for example, trisammonium hexachlororhodate(III). Others which are suitable are rhodium complexes such as rhodiumbiscarbonyl acetylacetonate, acetylacetonatobisethylenerhodium(I).

Rhodiumbiscarbonylacetylacetonate or rhodium acetate are preferably employed.

Examples of suitable cobalt compounds are cobalt(II) chloride, cobalt(II) sulfate, cobalt(II) carbonate, cobalt(II) nitrate, their amine or hydrate complexes, cobalt carbocyclates such as cobalt acetate, cobalt ethylhexanoate, cobalt naphthanoate and the cobalt caprolactamate complex. The carbonyl complexes of cobalt, such as dicobaltoctocarbonyl, tetracobaltdodecacarbonyl and hexacobalthexadecacarbonyl, may also be employed for this purpose.

The abovementioned cobalt, rhodium and ruthenium compounds are known in principle and are described sufficiently in the literature or else can be prepared by the skilled worker in analogy to the known compounds.

The hydroformylation can be carried out with addition of inert solvents or diluents or without such an addition. Examples of suitable inert additions are acetone, methyl ethyl ketone, cyclohexanone, toluene, xylene, chlorobenzene, methylene chloride, hexane, petroleum ether, acetonitrile and the high-boiling fractions obtained in the hydroformylation of the dimerization products.

If the aldehyde content of the resulting hydroformylation product is unduly high, this may be remedied simply by hydrogenation, for example using hydrogen in the presence of Raney nickel or using other catalysts which are known for hydrogenation reactions, in particular catalysts containing copper, zinc, cobalt, nickel, molybdenum, zirconium or titanium. Most of the aldehyde fraction present is hydrogenated to give alkanols. If the aldehyde fraction in the reaction mixture is to be virtually eliminated, this can be achieved, if desired, by a second hydrogenation process, for example using an alkali metal borohydride under particularly mild and economical conditions.

The pure $C_{13}$-alcohol mixture according to the invention can be obtained from the reaction mixture which results from the hydrogenation process by customary purification methods known to the skilled worker, in particular by fractional distillation.

As a rule, $C_{13}$-alcohol mixtures according to the invention have a mean degree of branching of from 1 to 4, preferably from 2.1 to 2.5, in particular from 2.2 to 2.4. The degree of branching is defined as the number of methyl groups in one molecule of the alcohol minus 1. The mean degree of branching is the statistical mean of the degrees of branching of the molecules of a sample. The mean number of methyl groups in the molecules of a sample can be determined readily by $^1H$-NMR spectroscopy. For this purpose, the signal area corresponding to the methyl protons in the $^1H$-NMR spectrum of a sample is divided by three and then divided by the signal area of the methylene protons if the $CH_2$—OH group divided by two.

Preferred within this embodiment, which is based on $C_{13}$-oxo alcohols, are in particular those alcohol alkoxylates which are either ethoxylated or which are block alkoxylates of the EO/PO type.

The degree of ethoxylation of the ethoxylated $C_{13}$-oxo alcohols to be used in accordance with the invention is, as a rule, 1 to 50, preferably 3 to 20 and in particular 3 to 10, mainly 4 to 10 and especially 5 to 10.

The degrees of alkoxylation of the EO/PO block alkoxylates to be used in accordance with the invention depends on the location of the blocks. If the PO blocks are located terminally, the ratio between EO units and PO units is, as a rule, at least 1, preferably 1:1 to 4:1 and in particular 1.5:1 to 3:1. The degree of ethoxylation here is, as a rule, 1 to 20, preferably 2 to 15 and in particular 4 to 10, and the degree of propoxylation is, as a rule, 1 to 20, preferably 1 to 8 and in particular 2 to 5. The total degree of alkoxylation, i.e. the total of EO and PO units, is, as a rule, 2 to 40, preferably 3 to 25 and in particular 6 to 15. If, in contrast, the EO blocks are located terminally, the ratio between PO blocks and EO blocks is less critical and is, as a rule, 1:10 to 3:1, preferably 1:1.5 to 1:6. In this case, the degree of ethoxylation is, as a rule, 1 to 20, preferably 2 to 15, in particular 4 to 10, and the degree of propoxylation is, as a rule, 0.5 to 10, preferably 0.5 to 6, in particular 1 to 4. As a rule, the total degree of alkoxylation is 1.5 to 30, preferably 2.5 to 21 and in particular 5 to 14.

In accordance with a further preferred embodiment, alcohol alkoxylates which are based on $C_{10}$-oxo alcohols are used.

Analogously to the term "$C_{13}$-oxo alcohol", which has already been explained, the term "$C_{10}$-oxo alcohols" represents $C_{10}$-alcohol mixtures whose main component is formed by at least one branched $C_{10}$-alcohol (isodecanol).

Suitable $C_{10}$-alcohol mixtures can generally be obtained by hydrogenation of hydroformylated trimeric propene. In particular, it is possible to proceed as follows:

a) propenes are brought into contact with a suitable catalyst for oligomerization,
b) a $C_9$-olefin fraction is isolated from the reaction mixture,
c) the $C_9$-olefin fraction is hydroformylated by reacton with carbon monoxide and hydrogen in the presence of a suitable catalyst, and
d) hydrogenated.

Particular embodiments of this procedure result in analogy to the embodiments described above for the hydrogenation of hydroformylated trimeric butene.

It follows from what has been said above that in particular the $C_{13}$-oxo alcohols or the $C_{10}$-oxo alcohols to be used in accordance with the invention are based on olefins which preexist in branched form. In other words, branchings cannot be attributed to the hydroformylation reaction alone, as would be the case in the hydroformylation of straight-chain olefins. This is why the degree of branching of alkoxylates to be used in accordance with the invention is, as a rule, greater than 1.

As a rule, the alkoxylates to be used in accordance with the invention have a relatively small contact angle. Especially preferred alkoxylates are those with a contact angle of less than 120°, preferably less than 100°, when determined in the manner known per se using an aqueous solution comprising 2% by weight of alkoxylate on a paraffin surface.

According to one aspect, the surface-active properties of the alkoxylates depend on the nature and distribution of the alkoxylate group. The surface tension, as can be determined by the "pendant drop" method, of alkoxylates to be used in accordance with the invention is preferably in a range of from 25 to 70 mN/m, in particular 28 to 50 mN/m, for a solution comprising 0.1% by weight of alkoxylate, and in a range of from 25 to 70 mN/m, in particular 28 to 45 mN/m, for a solution comprising 0.5% by weight of alkoxylate. Alkoxylates to be used in accordance with the invention thus qualify as amphiphilic substances.

Accordingly, the present invention also relates to compositions comprising (a) at least one active ingredient for the treatment of plants; and
(b) at least one alkoxylated branched alcohol.

It is advantageous when component (b) amounts to more than 1% by weight, preferably more than 5% by weight and in particular more than 10% by weight based on the total weight of the composition. On the other hand, it is expedient, as a rule, when component (b) amounts to less than 50% by weight, preferably less than 45% by weight and in particular less than 40% by weight based on the total weight of the composition.

The active ingredient (component (a)) can be selected among herbicides, fungicides, insecticides, acaricides, nematicides, and active ingredients which regulate plant growth.

Herbicidal crop protection compositions may comprise, for example, one or more of the following herbicidal crop protectants:

1,3,4-thiadiazoles such as buthidazole and cyprazole, amides such as allidochlor, benzoylpropethyl, bromobutide, chlorthiamid, dimepiperate, dimethenamid, diphenamid, etobenzanid, flamprop-methyl, fosamin, isoxaben, monalide, naptalame, pronamid, propanil, aminophosphoric acids such as bilanafos, buminafos, glufosinate-ammonium, glyphosate, sulfosate, aminotriazoles such as amitrol, anilides such as anilofos, mefenacet, aryloxyalkanoic acid such as 2,4-D, 2,4-DB, clomeprop, dichlorprop, dichlorprop-P, dichlorprop-P, fenoprop, fluroxypyr, MCPA, MCPB, mecoprop, mecoprop-P, napropamide, napropanilide, triclopyr, benzoic acids such as chloramben, dicamba, benzothiadiazinones such as bentazone, bleachers such as clomazone, diflufenican, fluorochloridone, flupoxam, fluridone, pyrazolate, sulcotrione, carbamates such as carbetamid, chlorbufam, chlorpropham, desmedipham, phenmedipham, vernolate, quinolinecarboxylic acids such as quinclorac, quinmerac, dichloropropionic acids such as dalapon, dihydrobenzofurans such as ethofumesate, dihydrofuran-3-one such as flurtamone, dinitroanilines such as benefin, butralin, dinitramin, ethalfluralin, fluchloralin, isopropalin, nitralin, oryzalin, pendimethalin, prodiamine, profluralin, trifluralin, dinitrophenols such as bromofenoxim, dinoseb, dinoseb-acetate, dinoterb, DNOC, minoterb-acetate, diphenyl ethers such as acifluorfen-sodium, aclonifen, bifenox, chlornitrofen, difenoxuron, ethoxyfen, fluorodifen, fluoroglycofen-ethyl, fomesafen, furyloxyfen, lactofen, nitrofen, nitrofluorfen, oxyfluorfen, dipyridyls such as cyperquat, difenzoquat-methylsulfate, diquat, paraquat-dichloride, imidazoles such as isocarbamid, imidazolinones such as imazamethapyr, imazapyr, imazaquin, imazethabenz-methyl, imazethapyr, oxadiazoles such as methazole, oxadiargyl, oxadiazon, oxiranes such as tridiphane, phenols such as bromoxynil, ioxynil, phenoxyphenoxypropionic esters such as clodinafop, cyhalofop-butyl, diclofop-methyl, fenoxaprop-ethyl, fenoxaprop-p-ethyl, fenthiaprop-ethyl, fluazifop-butyl, fluazifop-p-butyl, haloxyfop-ethoxyethyl, haloxyfop-methyl, haloxyfop-p-methyl, isoxapyrifop, propaquizafop, quizalofop-ethyl, quizalofop-p-ethyl, quizalofop-tefuryl, phenylacetic acids such as chlorfenac, phenylpropionic acids such as chlorophenprop-methyl, ppi active ingredients such as benzofenap, flumiclorac-pentyl, flumioxazin, flumipropyn, flupropacil, pyrazoxyfen, sulfentrazone, thidiazimin, pyrazoles such as nipyraclofen, pyridazines such as chloridazon, maleic hydrazide, norflurazon, pyridate, pyridinecarboxylic acids such as clopyralid, dithiopyr, picloram, thiazopyr, pyrimidyl ethers such as pyrithiobac-acid, pyrithiobac-sodium, KIH-2023, KIH-6127, sulfonamides such as flumetsulam, metosulam, triazolecarboxamides such as triazofenamid, uracils such as bromacil, lenacil, terbacil, furthermore benazolin, benfuresate, bensulide, benzofluor, butamifos, cafenstrole, chlorthal-dimethyl, cinmethylin, dichlobenil, endothall, fluorbentranil, mefluidide, perfluidone, piperophos.

Preferred herbicidal plant protectants are those of the sulfonylurea type such as amidosulfuron, azimsulfuron, bensulfuron-methyl, chlorimuron-ethyl, chlorsulfuron, cinosulfuron, cyclosulfamuron, ethametsulfuron-methyl, flazasulfuron, halosulfuron-methyl, imazosulfuron, metsulfuron-methyl, nicosulfuron, primisulfuron, prosulfuron, pyrazosulfuron-ethyl, rimsulfuron, sulfometuron-methyl, thifensulfuron-methyl, triasulfuron, tribenuron-methyl, triflusulfuron-methyl, tritosulfuron.

Preferred herbicidal plant protectants are furthermore those of the cyclohexenone type such as alloxydim, clethodim, cloproxydim, cycloxydim, sethoxydim and tralkoxydim.

Very especially preferred herbicidal active ingredients of the cyclohexenone type are: tepraloxydim (cf. AGROW, No. 243, 11.3.95, page 21, caloxydim) and 2-(1-[2-{4-chlorophenoxy}propyl-oxyimino]butyl)-3-hydroxy-5-(2H-tetrahydrothiopyran-3-yl)-2-cyclohexen-1-one, and of the sulfonylurea type: N-(((4-methoxy-6-[trifluoromethyl]-1,3,5-triazin-2-yl)amino)carbonyl)-2-(trifluoromethyl)benzenesulfonamide.

The fungicidal compositions comprise one or more of, for example, the following fungicidal active ingredients: sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfides, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis(thiocarbamoyl)disulfide;

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenylisopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)-phosphinyl]-3-phenyl-1,2,4-triazole, 2,3-dicyano-1,4-dithio-anthraquinone, 2-thio-1,3-dithiolo[4,5-b]quinoxaline, methyl 1-(butylcarbamoyl)-2-benzimidazolecarbamate, 2-methoxycarbonyl-aminobenzimidazole, 2-(2-furyl)benzimidazole, 2-(4-thiazolyl)-benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfodiamide, 5-ethoxy-3-trichloromethyl-1,2,3-thiadiazole, 2-thiocyanato-methylthiobenzothiazole, 1,4-dichloro-2,5-dimethoxybenzene, 4-(2-chlorophenylhydrazono)-3-methyl-5-isoxazolone, pyridine-2-thiol 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis-1-(2,2,2-trichloroethyl)formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butyl-phenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS,3RS)-1-[3-(2-chlorophenyl)-2-(4-fluorophenyl)oxiran-2-ylmethyl]-1H-1,2,4-triazole, α-(2-chlorophenyl)-α-(4-chloro-phenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxy-carbonyl-2-thioureido)benzene, strobilurins such as methyl E-methoxyimino-[α-(o-tolyloxy)-o-tolyl]acetate, methyl E-2-{2-[6-(2-cyanophenoxy)pyrimidin-4-yloxy]phenyl}-3-methoxyacrylate, N-methyl-E-methoxyimino-[α-(2-phenoxyphenyl)]acetamide, N-methyl-E-methoxyimino-[α-(2,5-dimethylphenoxy)-o-tolyl]acetamide, anilinopyrimidines such as N-(4,6-dimethylpyrimidin-2-yl)aniline, N-[4-methyl-6-(1-propynyl)pyrimidin-2-yl]aniline, N-[4-methyl-6-cyclopropylpyrimidin-2-yl]aniline, phenylpyrroles such as 4-(2,2-difluoro-1,3-benzodioxol-4-yl)-pyrrole-3-carbonitrile, cinnamamides such as 3-(4-chlorophenyl)-3-(3,4-dimethoxyphenyl)-acryloylmorpholine, and a variety of fungicides such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)-alanine methyl ester, N-(2,6-dimethylphenyl)-N-chloroacetyl-D,L-2-aminobutyrolactone, DL-N-(2,6-dimethylphenyl)-N-(phenyl-acetyl)alanine methyl ester, 5-methyl-5-vinyl-3-(3,5-dichlorophenyl)-2,4-dioxo-1,3-oxazolidine, 3-[3,5-dichlorophenyl-(5-methyl-5-methoxymethyl]-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]-acetamide, 1-[2-(2,4-dichlorophenyl)pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoro-methyl-3-chloro-2-aminopyridine, 1-((bis(4-fluorophenyl)methyl-silyl)methyl)-1H-1,2,4-triazole.

Useful growth regulators are, for example, the group of the gibberellins. These include, for example, the gibberellins $GA_1$, $GA_3$, $GA_4$, $GA_5$ and $GA_7$ and the like, and the corresponding exo-16,17-dihydrogibberellins and the derivatives thereof, for example the esters with $C_1$-$C_4$-carboxylic acids. Preferred in accordance with the invention is exo-16,17-dihydro-$GA_5$-13-acetate.

In accordance with one embodiment of the present invention, the active ingredient component (a) consists essentially of one or more of the following preferred active ingredients: bentazone, difenzoquat, pendimethalin, quinclorac, cycloxydim, quinmerac, sethoxydim, cinidon-ethyl, mecoprop, mecoprop-P, dichlorprop, chloridazon, dicamba, metobromuron, profoxydim, tritosulfuron, diflufenzopyr, s-dimethenamid, cyanazine, picolinafen, cyclosulfamuron, imazamethabenz-methyl, imazaquin, acifluorfen, nicosulfuron, sulfur, dithianon, tridemorph, metiram, nitrothal-isopropyl, thiophanate-methyl, metholachlor, triforine, cerbendazim, vinclozolin, dodine, fenpropimorph, epoxiconazole, kresoxim-methyl, pyraclostrobin, dimoxystrobin, cyazofamid, fenoxalin, dimethomorph, metconazole, dimethoate, chlorfenvinphos, phorate, fenbutatin oxide, chrorfenapyr, simazine, bensulforon, flufenoxuron, terflubenzuron, alpha-cypermetrin, cypermethrin, hydramehylnon, terbufos, temephos, halofenozide, flocoumafen, triazamate, flucythrinate, hexythiazox, dazomet, chlorocholin chloride, mepiquat-chloride, prohexadion-calcium, or of one or more of the following very especially preferred active ingredients: metazachlor, paraquat, glyphosate, imazethaphyr, tepraloxydim, imazapic, imazamox, acetochlor, atrazine, tebufenpyrad, trifluralin, pyridaben.

In particular, the present invention relates to compositions comprising high percentages of active ingredient (concentrates). Thus, as a rule, component (a) amounts to more than 10% by weight, preferably more than 15% by weight and in particular more than 20% by weight of the total weight of the composition. On the other hand, as a rule, component (a) expediently amounts to less than 80% by weight, preferably less than 70% by weight and in particular less than 60% by weight of the total weight of the composition.

Besides, the formulations according to the invention may comprise auxiliaries and/or additives which are conventionally used in the preparation of formulations used for agrotechnical applications, in particular in the field of crop protection. These include, for example, surfactants, dispersants, wetters, thickeners, organic solvents, cosolvents, antifoams, carboxylic acids, preservatives, stabilizers and the like.

In accordance with a particular embodiment of the present invention, the compositions comprise at least one (further) surfactant as surface-active component (c). In this context, the term "surfactant" refers to interface- or surface-active agents.

Component (c) is added in particular in the form of a dispersant or emulsifier, mainly for dispersing a solid in suspension concentrates. Moreover, parts of component (c) may act as wetters.

Surfactants which can be used in principle are anionic, cationic, amphoteric and nonionic surfactants, including polymer surfactants and surfactants with heteroatoms in the hydrophobic group.

The anionic surfactants include, for example, carboxylates, in particular alkali metal, alkaline earth metal and ammonium salts of fatty acids, for example potassium stearate, which are usually also referred to as soaps; acyl glutamates; sarcosinates, for example sodium lauroyl sarcosinate; taurates; methylcelluloses; alkyl phosphates, in particular alkyl esters of mono- and diphosphoric acid; sulfates, in particular alkyl sulfates and alkyl ether sulfates; sulfonates, furthermore alkylsulfonates and alkylarylsulfonates, in particular alkali metal, alkaline earth metal and ammonium salts of arylsulfonic acids and of alkyl-substituted arylsulfonic acids, alkylbenzenesulfonic acids, such as, for example, lignosulfonic acid and phenolsulfonic acid, naphthalene- and dibutylnaphthalenesulfonic acids, or dodecylbenzenesulfonates, alkylnaphthalenesulfonates, alkyl methyl ester sulfonates, condensates of sulfonated naphthalene and derivatives thereof with formaldehyde, condensates of naphthalenesulfonic acids, phenol- and/or phenolsulfonic acids with formaldehyde or with formaldehyde and urea, mono- or dialkyl sulfosuccinates; and protein hydrolyzates and lignin-sulfite waste liquors. The abovementioned sulfonic acids are advantageously used in the form of their neutral or, if appropriate, basic salts.

The cationic surfactants include, for example, quaternized ammonium compounds, in particular alkyltrimethylammonium halides, dialkyldimethylammonium halides, alkyltrimethylammonium alkyl sulfates, dialkyldimethylammonium alkyl sulfates and pyridine and imidazoline derivatives, in particular alkylpyridinium halides.

The nonionic surfactants include, for example, further alkoxylates, mainly ethoxylates, and nonionic surfactants, in particular

- fatty alcohol polyoxyethylene esters, for example lauryl alcohol polyoxyethylene ether acetate,
- alkyl polyoxyethylene ethers and alkyl polyoxypropylene ethers, for example of linear fatty alcohols, alkylaryl alcohol polyoxyethylene ethers, for example octylphenol polyoxyethylene ether,
- alkoxylated animal and/or vegetable fats and/or oils, for example corn oil ethoxylates, castor oil ethoxylates, tallow fat ethoxylates,
- glycerol esters such as, for example, glycerol monostearate,
- fatty alcohol alkoxylates and oxo alcohol alkoxylates, in particular of the linear type $R_5O—(R_3O)_r(R_4O)_sR_{20}$ where $R_3$ and $R_4$ independently of one another=$C_2H_4$, $C_3H_6$, $C_4H_8$ and $R_{20}$=H, or $C_1$-$C_{12}$-alkyl, $R_5$=$C_3$-$C_{30}$-alkyl or $C_6$-$C_{30}$-alkenyl, r and s independently of one another are 0 to 50, where one of these must be other than 0, and oleyl alcohol polyoxyethylene ether,
- alkylphenol alkoxylates such as, for example, ethoxylated isooctylphenol, octylphenol or nonylphenol, tributylphenyl polyoxyethylene ethers,
- fatty amine alkoxylates, fatty acid amide alkoxylates and fatty acid diethanolamide alkoxylates, in particular their ethoxylates,
- sugar surfactants, sorbitol esters such as, for example, sorbitan fatty acid esters (sorbitan monooleate, sorbitan tristearate), polyoxyethylene sorbitan fatty acid esters, alkylpolyglycosides, N-alkylgluconamides,
- alkylmethyl sulfoxides,
- alkyldimethylphosphine oxides such as, for example, tetradecyldimethylphosphine oxide.

The amphoteric surfactants include, for example, sulfobetaines, carboxybetaines and alkyldimethylamine oxides, for example tetradecyldimethylamine oxide.

The polymeric surfactants include, for example, di-, tri- and multi-block polymers of the type (AB)x, ABA and BAB, for example optionally end-capped ethylene oxide/propylene oxide block copolymers, for example ethylenediamine-EO/PO block copolymers, polystyrene block polyethylene oxide, and AB comb polymers, for example polymethacrylate comb polyethylene oxide.

Further surfactants to be mentioned in the present context by way of example are perfluoro surfactants, silicone surfactants, for example polyether-modified siloxanes, phospholipids such as, for example lecithin or chemically modified lecithins, amino acid surfactants, for example N-lauroylglutamate, and surface-active homo- and copolymers, for example polyvinylpyrrolidone, polyacrylic acids in the form of their salts, polyvinyl alcohol, polypropylene oxide, polyethylene oxide, maleic anhydride/isobutene copolymers and vinylpyrrolidone/vinyl acetate copolymers.

Unless specified, the alkyl chains of the abovementioned surfactants are linear or branched radicals, usually having 8 to 20 carbon atoms.

The further surfactant as regards component (c) is preferably selected from among nonionic surfactants. Preferred among the nonionic surfactants are, in particular, those with HLB values ranging from 2 to 16, preferably from 5 to 16, in particular from 8 to 16.

As a rule, component (c)—if present—amounts to less than 50% by weight, preferably less than 15% by weight and in particular less than 5% by weight of the total weight of the composition.

In accordance with a particular embodiment of the present invention, the compositions comprise at least one further auxiliary as component (d).

Component (d) can fulfill a variety of purposes. Suitable auxiliaries are chosen in the customary manner by the skilled worker to suit the requirements.

For example, further auxiliaries are selected from among (d1) solvents or diluents;

(d2) emulsifiers, delayed-release agents, pH buffers, antifoams.

Besides water, the compositions may comprise further solvents of soluble components or diluents of insoluble components of the composition.

Examples which are useful in principle are mineral oils, synthetic oils, vegetable oils and animal oils, and low-molecular-weight hydrophilic solvents such as alcohols, ethers, ketones and the like.

Those which must therefore be mentioned are, firstly, aprotic or apolar solvents or diluents, such as mineral oil fractions of medium to high boiling point, for example kerosene and diesel oil, furthermore coal tar oils, hydrocarbons, paraffin oils, for example $C_8$- to $C_{30}$-hydrocarbons of the n- or isoalkane series or mixtures of these, optionally hydrogenated or partially hydrogenated aromatics or alkylaromatics from the benzene or naphthalene series, for example aromatic or cycloaliphatic $C_7$- to $C_{18}$-hydrocarbon compounds, aliphatic or aromatic carboxylic acid esters or dicarboxylic acid esters, or fats or oils of vegetable or animal origin, such as mono-, di- and triglycerides, in pure form or in the form of a mixture, for example in the form of oily extracts of natural materials, for example olive oil, soya oil, sunflower oil, castor oil, sesame seed oil, corn oil, groundnut oil, rapeseed oil, linseed oil, almond oil, castor oil, safflower oil, and their raffinates, for example hydrogenated or partially hydrogenated products thereof and/or their esters, in particular the methyl and ethyl esters.

Examples of $C_8$- to $C_{30}$-hydrocarbons of the n- or isoalkane series are n- and isooctane, -decane, -hexadecane, -octadecane, -eicosane, and preferably hydrocarbon mixtures such as liquid paraffin (technical-grade liquid paraffin may comprise up to approximately 5% aromatics) and a $C_{18}$-$C_{24}$ mixture which is commercially available from Texaco under the name Spraytex oil.

The aromatic or cycloaliphatic $C_7$ to $C_{18}$ hydrocarbon compounds include, in particular, aromatic or cycloaliphatic solvents from the series of the alkylaromatics. These compounds may be unhydrogenated, partially hydrogenated or fully hydrogenated. Such solvents include, in particular, mono-, di- or trialkylbenzenes, mono-, di- or trialkyl-substituted tetralins and/or mono-, di-, tri- or tetraalkyl-substituted naphthalenes (alkyl is preferably $C_1$-$C_6$-alkyl). Examples of such solvents are toluene, o-, m-, p-xylene, ethylbenzene, isopropylbenzene, tert-butylbenzene and mixtures, such as the Exxon products sold under the names Shellsol and Solvesso, for example Solvesso 100, 150 and 200.

Examples of suitable monocarboxylic esters are oleic esters, in particular methyl oleate and ethyl oleate, lauric esters, in particular 2-ethylhexyl laurate, octyl laurate and isopropyl laurate, isopropyl myristate, palmitic esters, in particular 2-ethylhexyl palmitate and isopropyl palmitate, stearic esters, in particular n-butyl stearate and 2-ethylhexyl 2-ethylhexanoate.

Examples of suitable dicarboxylic esters are adipic esters, in particular dimethyl adipate, di-n-butyl adipate, di-n-octyl adipate, di-iso-octyl adipate, also referred to as bis(2-ethylhexyl) adipate, di-n-nonyl adipate, diisononyl adipate and ditridecyl adipate; succinic esters, in particular di-n-octyl succinate and diisooctyl succinate, and di(isononyl)cyclohexane 1,2-dicarboxylate.

As a rule, the above-described aprotic solvents or diluents amount to less than 80% by weight, preferably less than 50% by weight and in particular less than 30% by weight of the total weight of the composition.

Some of these aprotic solvents or diluents may also have adjuvant properties, that is to say in particular synergistic properties. This applies in particular to said mono- and dicarboxylic esters. From this point of view, such adjuvants, perhaps in the form of a part of a further formulation (stand-alone product), may also be mixed with the alcohol alkoxylates according to the invention or with compositions comprising them at an expedient point in time, as a rule shortly prior to application.

Secondly, solvents or diluents which must be mentioned are protic or polar solvents or diluents, for example $C_2$-$C_8$-monoalcohols such as ethanol, propanol, isopropanol, butanol, isobutanol, tert-butanol, cyclohexanol and 2-ethylhexanol, $C_3$-$C_8$-ketones such as diethyl ketone, t-butyl methyl ketone and cyclohexanone, and aprotic amines such as N-methyl- and N-octylpyrrolidone.

As a rule, the above-described protic or polar solvents or diluents amount to less than 80% by weight, preferably less than 50% by weight and in particular less than 30% by weight of the total weight of the composition.

Sedimentation inhibitors may also be used, in particular for suspension concentrates. Their main purpose is rheological stabilization. Products which must be mentioned in this context are, in particular, mineral products, for example bentonites, talcites and herctorites.

Other additions which may be useful can be found for example among mineral salt solutions which are employed for alleviating nutritional and trace element deficiencies, non-phytotoxic oils and oil concentrates, antidrift reagents, antifoams, in particular the silicone type products, for example Silicon SL, which is sold by Wacker, and the like.

The formulations may be present in the form of an emulsifiable concentrate (EC), a suspoemulsion (SE), an oil-in-water emulsion (O/W), a water-in-oil emulsion (W/O), an aqueous suspension concentrate, an oil suspension concentrate (SC), a microemulsion (ME) and the like.

The compositions can be prepared in the manner known per se. To this end, at least some of the components are combined. It must be taken into consideration that products, in particular commercially available products, can be used whose constituents may contribute to different components. For example, a specific surfactant can be dissolved in an aprotic solvent, so that this product can contribute to different components. Furthermore, it is also possible in some circumstances for minor amounts of less desired substances to be introduced together with commercially available products. As a rule, the products which have been combined to a mixture must then be mixed thoroughly with each other to give a homogeneous mixture and, if appropriate, milled, for example in the case of suspensions.

Mixing can be carried out in a manner known per se, for example by homogenizing with suitable devices such as KPG stirrers or magnetic stirrers.

Milling, too, is a process which is known per se. The milling elements used can be made of glass or can be other mineral or metallic milling elements, as a rule in a size of from 0.1-30 mm and in particular 0.6-2 mm. As a rule, the mixture is comminuted until the desired particle size has been achieved.

In general, milling may be carried out as a recirculation process, i.e. by continuously cycling an SC, or as a batch process, i.e. the complete and repeated processing of a batch.

Milling can be effected with conventional ball mills, bead mills or agitated mills, for example in a Dynomühle mill (Bachofen), with batch sizes of, for example, from 0.5 up to 1 liter in what is known as a batch operation. After several passes, in particular 4 to 6 passes (the suspension being pumped through the mill with the aid of a peristaltic pump), evaluation under the microscope reveals mean particle sizes of from 0.5 to 10 μm.

As a rule, the compositions are diluted in the customary manner prior to use to obtain a form which is suitable for application. Dilution with water or else aprotic solvents, for example by the tank mix method, is preferred. The use in the form of a slurry preparation is preferred. The application may be pre- or post-emergence. Post-emergence application results in particular advantages.

The use according to the invention also encompasses the use of the alkoxylates according to the invention as “stand-alone” products. To this end, the alkoxylates are prepared in a suitable manner and added shortly before use to the composition to be applied.

Particular advantages result mainly when carrying out a spray treatment. A customary spray mixture to be used as a tank mix involves diluting the compositions according to the invention which already comprise at least one alkoxylated branched alcohol—or further plant treatment products with addition of at least one alkoxylated branched alcohol as “stand-alone” product—with water to apply, per hectare, approximately 0.01 to 10, preferably approximately 0.05 to 5, in particular 0.1 to 1, kg of at least one alkoxylate according to the invention.

For the purposes of the present description, the terms alkyl encompasses straight-chain or branched hydrocarbon groups such as methyl, ethyl, n-propyl, i-propyl, n-butyl, i-butyl, sec-butyl, t-butyl, n-pentyl, n-hexyl, n-octyl, 2-ethylhexyl, n-nonyl, isononyl, n-decyl, isodecyl, n-undecyl, isoundecyl, n-dodecyl, isododecyl, n-tridecyl, isotridecyl, stearyl, n-eicosyl, preferably—unless otherwise specified—having 1 to 8, in particular 1 to 6 and especially preferably 1 to 4 carbon atoms in the case of short-chain radicals and 5 to 30, in particular 12 to 24 and especially preferably 8 to 20 carbon atoms in the case of long-chain radicals. The branched long-chain radicals include mainly 2-ethylhexyl, isononyl, isodecyl such as 2-propylheptyl, isoundecyl, isododecyl, and isotridecyl such as 2,4,8-tetramethyl-1-nonyl, 3,4,6,8-tetramethyl-1-nonyl and 5-ethyl-4,7-dimethyl-1-nonyl.

For the purposes of the present description, quantities generally refer to the total weight of a composition, unless otherwise specified. As a rule, the term “essentially” refers in accordance with the invention to a percentage of at least 80%, preferably at least 90% and in particular at least 95%.

The invention is illustrated in greater detail by the examples which follow:

PREPARATION EXAMPLES

Reference Examples 1 to 5

Preparation of the Alkoxylates (a) to (e)

Reference Example 1

2-Propylheptanol+7 EO (a)

711 g of 2-propylheptanol (corresponding to 4.5 mol) together with 2.0 g of potassium hydroxide as alkoxylation catalyst were introduced into an autoclave. After a dehydration phase, 1386 g of ethylene oxide (corresponding to 31.5 mol) were passed in continuously at 150° C. To complete the reaction, stirring was continued for 1 hour at the same temperature. This gave 2080 g of the abovementioned product (a).

Reference Example 2 i-Tridecanol (Basis: Trimeric Butene)+6 EO+3 PO (b)

700 g of i-tridecanol (corresponding to 3.5 mol) together with 4.0 g of potassium hydroxide as alkoxylation catalyst were introduced into an autoclave. After a dehydration phase, 924 g of ethylene oxide (corresponding to 21.0 mol) were passed in continuously at 110 to 120° C. To complete the reaction, stirring was continued for 1 hour at the same temperature. The temperature was then raised to 150° C., and 609 g of propylene oxide (corresponding to 10.5 mol) were added continuously to the reactor. When the pressure was constant, the temperature was held for two hours to complete the reaction. This gave 2210 g of the abovementioned product (b).

Reference Example 3 i-Decanol+10 EO+1.5 Pentene Oxide (c)

474 g of i-decanol (corresponding to 3.0 mol) together with 4.5 g of potassium hydroxide as alkoxylation catalyst were introduced into an autoclave. After a dehydration phase, 1320 g of ethylene oxide (corresponding to 30.0 mol) were passed in continuously at 10 to 120° C. To complete the reaction, stirring was continued for 1 hour at the same temperature. The temperature was then raised to 160° C., and 387 g of pentene oxide (corresponding to 4.5 mol) were added continuously to the reactor. When the pressure was constant, the temperature was held for two hours to complete the reaction. This gave 2180 g of the abovementioned product (c).

Reference Example 4 i-Decanol+3 EO (d)

1106 g of i-decanol (corresponding to 7.0 mol) together with 1.0 g of potassium hydroxide as alkoxylation catalyst were introduced into an autoclave. After a dehydration phase, 924 g of ethylene oxide (corresponding to 21.0 mol) were passed in continuously at 150° C. To complete the reaction, stirring was continued for 1 hour at the same temperature. This gave 2010 g of the abovementioned product (d).

Reference Example 5 i-Tridecanol (Basis: Trimeric Butene)+3 EO (e)

1200 g of i-tridecanol (corresponding to 6.0 mol) together with 2.0 g of potassium hydroxide as alkoxylation catalyst were introduced into an autoclave. After a dehydration phase, 792 g of ethylene oxide (corresponding to 18.0 mol) were passed in continuously at 150° C. To complete the reaction, stirring was continued for 1 hour at the same temperature. This gave 1970 g of the abovementioned product (e).

Example 1

Herbicidal Efficacy of the Bentazone Formulations

The alkoxylates were applied by the tank mix method together with Basagran (480 g/l bentazone) or BAS 635 H (71.4% by weight of tritosulfuron). The application rate per ha was 0.250 kg of bentazone or 8 g/ha tritosulfuron and 0.125 kg of a.s./ha alkoxylate according to the invention or 0.250 kg/ha comparative adjuvant Atplus 411F (mineral oil/surfactant mixture; Uniqema). The herbicidal effect was assessed in a greenhouse experiment. The test plant used was white goosefoot (Chenepodium album; CHEAL) and the common morningglory (Pharbitis album; PHAAL).

The plants were sown directly or pricked out at a rate of 3-15 plants per pot. When the active ingredient was applied, the plants were 5-16 cm in height. The test containers used were plastic pots containing loamy sand and approximately 3% humus as substrate. The surfactants were applied by the tank mix method by spray application post-emergence in an automated spray cabinet with a water application rate of 400 liters per hectare. The experimental period was 6 days to 4 weeks. Evaluation was carried out using a scale of from 0% to 100%. 0% means no damage, 100% means complete damage.

The results of the assessment are compiled in tables 1 and 2 which follow.

TABLE 1

| Adjuvant | Bentazone (kg/ha) | Adjuvant (kg/ha) | CHEAL |
|---|---|---|---|
| — | 0.250 | — | 23% |
| a | 0.250 | 0.125 | 92% |
| b | 0.250 | 0.125 | 93% |
| c | 0.250 | 0.125 | 92% |
| d | 0.250 | 0.125 | 92% |
| e | 0.250 | 0.125 | 96% |
| Comparison | 0.250 | 0.250 | 50% |

TABLE 2

| Adjuvant | Tritosulfuron (kg/ha) | Adjuvant (kg/ha) | CHEAL | PHAAL |
|---|---|---|---|---|
| — | 0.250 | — | 35% | 48% |
| a | 0.250 | 0.125 | 90% | 65% |
| b | 0.250 | 0.125 | 92% | 65% |
| c | 0.250 | 0.125 | 90% | 68% |
| d | 0.250 | 0.125 | 92% | 65% |
| e | 0.250 | 0.125 | 90% | 73% |
| Comparison | 0.250 | 0.250 | 90% | 62% |

It can be seen clearly that formulations with alkoxylate according to the invention are considerably more effective than the comparative formulation without adjuvant, or than the comparative formulation which just contain Atplus 411 F instead of alkoxylates according to the invention.

We claim:

1. A composition comprising (a) at least one active ingredient for the treatment of plants, and (b) at least one alkoxylated 2-propylheptanol of the formula (I)

$$R—O—(C_mH_{2m}O)_x—(C_nH_{2n}O)_y—(C_pH_{2p}O)_z—H \quad (I)$$

in which

R is 2-propylheptyl;

m, n, p independently of one another are 2 or 3;

x+y+z has a value of 1 to 100.

2. The composition claimed in claim 1, wherein m is 2, the value of x is greater than zero and z is zero.

3. The composition claimed in claim 2, wherein y is zero.

4. The composition claimed in claim 2, wherein y is zero and the value of x is from 3 to 10.

5. The composition claimed in claim 2, wherein n is 3 and the value of y is greater than zero.

6. The method ac composition claimed in claim 5, wherein the ratio of x to y is from 1:1 to 4:1.

7. The composition claimed in claim 5, wherein the ratio of x to y is from 1.5:1 to 3:1.

8. The composition claimed in claim 5, wherein the value of x is from 4 to 10.

9. The composition claimed in claim 5, wherein the value of y is from 2 to 5.

10. The composition claimed in claim 5, wherein the total value of x+y is from 6 to 15.

11. The composition claimed in claim 5, wherein the value of x is from 4 to 10, the value of y is from 2 to 5, the ratio of x to y is from 1.5:1 to 3:1, and the total value of x+y is from 6 to 15.

12. The composition claimed in claim 1, wherein m is 2, n is 3, p is 2, and the values of x, y and z is in each case greater than zero.

13. The method as composition claimed in claim 1, wherein m is 3, n is 2, the value of x is greater than zero, the value of y is greater than zero and z is zero.

14. The composition claimed in claim 13, wherein the ratio of x to y is from 3:1 to 1:10.

15. The composition claimed in claim 13, wherein the ratio of x to y is from 1.5:1 to 1:6.

16. The composition claimed in claim 13, wherein the value of x is from 1 to 4.

17. The composition claimed in claim 13, wherein the value of y is from 4 to 10.

18. The composition claimed in claim 13, wherein the total value of x+y is from 5 to 14.

19. The composition claimed in claim 13, wherein the value of x is from 1 to 4, the value of y is from 4 to 10, the ratio of x to y is from 1.5:1 to 1:6, and the total value of x+y is from 5 to 14.

20. The composition claimed in claim 1, wherein component (b) amounts to more than 5% by weight based on the total weight of the composition.

21. The composition claimed in claim 1, wherein component (b) amounts to more than 10% by weight based on the total weight of the composition.

22. The composition claimed in claim 1, wherein the active ingredient is selected from bentazone, tritosulfuron, fenpropimorph, epoxiconazole, kresoxim-methyl, pyraclostrobin, dimethomorph and metconazole.

23. A method for the treatment of plants, said method comprising applying to the plants an active agent for the treatment of plants and an alkoxylated 2-propylheptanol of the formula (I)

$$R—O—(C_mH_{2m}O)_x—(C_nH_{2n}O)_y—(C_pH_{2p}O)_zH \quad (I)$$

in which

R is 2-propylheptyl;

m, n, p independently of one another are an integer from 2 to 16;

x+y+z have a value of 1 to 100, as adjuvant.

24. The method of claim 23 wherein the efficacy of said active agent for the treatment of plants is improved.

25. The method of claim 24, wherein the efficacy of the active ingredient is improved through better uptake of the active ingredient by the plant.

26. The method of claim 25, wherein uptake of the active ingredient takes place via a leaf or leaves of the plant.

27. The method of claim 23 in plant cultivation, in agriculture or in horticulture.

28. The method of claim 23, wherein the alkoxylated 2-propylheptanol is applied post-emergence.

29. The method of claim 23, wherein the alkoxylated 2-propylheptanol is applied by spraying on the plants.

30. The method of claim 29, wherein the alkoxylated 2-propylheptanol is applied as a tank additive.

* * * * *

UNITED STATES PATENT AND TRADEMARK OFFICE

CERTIFICATE OF CORRECTION

PATENT NO. : 8,129,312 B2
APPLICATION NO. : 10/512422
DATED : March 6, 2012
INVENTOR(S) : Berghaus et al.

It is certified that error appears in the above-identified patent and that said Letters Patent is hereby corrected as shown below:

In Claim 13, Column 24, line 20:
The phrase "The method as composition claimed"
should read --The composition claimed--

Signed and Sealed this
Eighteenth Day of September, 2012

David J. Kappos
*Director of the United States Patent and Trademark Office*